United States Patent
Naker et al.

(10) Patent No.: US 11,555,729 B2
(45) Date of Patent: *Jan. 17, 2023

(54) INFUSION MANAGEMENT PLATFORM WITH INFUSION DATA GROUPING LOGIC

(71) Applicant: CareFusion 303, Inc., San Diego, CA (US)

(72) Inventors: Sachin B. Naker, San Diego, CA (US); Tim Riddle, San Diego, CA (US)

(73) Assignee: Carefusion 303, Inc., San Diego, CA (US)

( * ) Notice: Subject to any disclaimer, the term of this patent is extended or adjusted under 35 U.S.C. 154(b) by 532 days.

This patent is subject to a terminal disclaimer.

(21) Appl. No.: 16/704,885

(22) Filed: Dec. 5, 2019

(65) Prior Publication Data

US 2020/0194105 A1 Jun. 18, 2020

Related U.S. Application Data

(63) Continuation of application No. 15/164,761, filed on May 25, 2016, now Pat. No. 10,503,871, which is a continuation of application No. 13/802,397, filed on Mar. 13, 2013, now Pat. No. 9,390,235.

(51) Int. Cl.

| | | |
|---|---|---|
| *G01F 22/00* | (2006.01) | |
| *G16H 20/17* | (2018.01) | |
| *G16H 20/40* | (2018.01) | |
| *G16H 40/63* | (2018.01) | |
| *G16H 20/30* | (2018.01) | |
| *G16H 40/67* | (2018.01) | |
| *A61M 5/14* | (2006.01) | |

(52) U.S. Cl.
CPC ............. *G01F 22/00* (2013.01); *G16H 20/17* (2018.01); *G16H 20/30* (2018.01); *G16H 20/40* (2018.01); *G16H 40/63* (2018.01); *G16H 40/67* (2018.01); *A61M 5/14* (2013.01); *A61M 5/1409* (2013.01); *A61M 2205/3584* (2013.01); *A61M 2205/3592* (2013.01)

(58) Field of Classification Search
CPC ........ G16H 20/17; G16H 20/40; G16H 20/30; G16H 40/67; G16H 40/63; G01F 22/00
See application file for complete search history.

(56) References Cited

U.S. PATENT DOCUMENTS

| | | |
|---|---|---|
| 5,317,506 A | 5/1994 | Coutre et al. |
| 5,795,327 A | 8/1998 | Wilson et al. |
| 6,775,577 B2 | 8/2004 | Crnkovich et al. |
| 8,291,337 B2 | 10/2012 | Gannin et al. |
| 9,690,909 B2 | 6/2017 | Stewart et al. |
| 2002/0040208 A1 | 4/2002 | Flaherty et al. |
| 2003/0140928 A1 | 7/2003 | Bui et al. |
| 2004/0055611 A1 | 3/2004 | Penny et al. |
| 2005/0005242 A1 | 1/2005 | Hoyle |
| 2005/0055242 A1 | 3/2005 | Bello et al. |
| 2005/0055244 A1 | 3/2005 | Mullan et al. |
| 2017/0274141 A1 | 9/2017 | Stewart et al. |

FOREIGN PATENT DOCUMENTS

| | | |
|---|---|---|
| CN | 1618075 A | 5/2005 |
| JP | 2002-183302 A | 6/2002 |
| JP | 2002-334153 A | 11/2002 |
| JP | 2005-028102 A | 2/2005 |
| JP | 2005-208856 A | 8/2005 |

*Primary Examiner* — Jerry Lin
(74) *Attorney, Agent, or Firm* — Mintz Levin Cohn Ferris Glovsky and Popeo, P.C.

(57) ABSTRACT

An infusion management platform can determine, based on one or more infusion events, whether to group infusions or segments of infusions. Related apparatus, systems, techniques and articles are also described.

20 Claims, 4 Drawing Sheets

INFUSION MANAGEMENT PLATFORM WITH INFUSION DATA GROUPING LOGIC

CROSS-REFERENCE TO RELATED APPLICATIONS

This application is a continuation of U.S. patent application Ser. No. 15/164,761, filed May 25, 2016 (now issued as U.S. Pat. No. 10,503,871), which is a continuation of U.S. patent application Ser. No. 13/802,397, filed Mar. 13, 2013 (now issued as U.S. Pat. No. 9,390,235), the contents of which are herein incorporated by reference in their entirety.

TECHNICAL FIELD

The subject matter described herein relates to an infusion management platform for tracking volume of fluid/medication within infusion containers.

BACKGROUND

In clinical settings, infusions for administration to a patient may be given by route of: intravenous (IV), subcutaneous, intra-arterial, epidural, enteral or irrigation of fluid spaces. These infusions may be delivered via a large volume pump, a syringe or by patient controlled analgesia. Infusions are often controlled by the hospital pharmacy and the pharmacy or prescriber can typically specify the volume of diluent that each infusion contains. It is common practice for nurses who program the infusion at the patient's bedside to program the Volume To Be Infused (VTBI) for an amount less than the entire container volume. Nurses may program the infusion to be given in segments by programming multiple VTBIs until the entire container volume has been administered. Difficulties can arise when associating such VTBIs with a particular medication container.

SUMMARY

In one aspect, data is received that characterizes a first infusion of fluid into a patient from a container by an infusion module. The first infusion can have an associated first order identifier and an associated first volume infused. Thereafter, an infusion event is identified that interrupts or terminates the infusion. Subsequently, data is received that characterizes a second infusion of fluid into the patient by the infusion module. The second infusion has an associated second volume to be infused. It is then determined whether the second volume to be infused is less than a pre-defined percentage of the first volume infused. The first order identifier is assigned to the second infusion if the second volume to be infused is less than a pre-defined percentage of the first volume infused. Otherwise, the second order identifier (which is different from the first order identifier) is assigned to the second infusion if the second volume to be infused is greater than a pre-defined percentage of the first volume to be infused.

The order identifier assignment can be based on a determination of whether the second infusion has characteristics matching the first infusion. Sample characteristics include one or more of, a profile name, a patient name, an infusion module identifier, a patient care unit identifier, an infusion type, and a drug name.

Furthermore, data can be provided (e.g., displayed, loaded, stored, transmitted, etc.) that characterizes the order identifier assignment.

In a further interrelated aspect, a method can comprise: receiving first data characterizing a first infusion of fluid into a patient from a container by an infusion module, the first infusion having an associated first order identifier and an associated first volume infused, the first data comprising one or more characteristics selected from a group consisting of: a profile name, a patient name, an infusion module identifier, a patient care unit identifier, an infusion type, and a drug name; identifying an infusion event interrupting or terminating the infusion; receiving second data characterizing a second infusion of fluid into the patient by the infusion module, the second infusion having an associated second volume to be infused, the second data comprising one or more characteristics selected from a group consisting of: a profile name, a patient name, an infusion module identifier, a patient care unit identifier, an infusion type, and a drug name; determining that at least one of the characteristics in the first data matches at least one of the characteristics in the second data; determining whether the second volume to be infused is less than a pre-defined percentage of the first volume infused; and assigning the first order identifier to the second infusion if the second volume to be infused is less than a pre-defined percentage of the first volume infused; or assigning a second order identifier, different from the first order identifier, to the second infusion if the second volume to be infused is greater than a pre-defined percentage of the first volume to be infused.

Computer program products are also described that comprise non-transitory computer readable media storing instructions, which when executed one or more data processors of one or more computing systems, causes at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The subject matter described herein provides many advantages. For example, the current subject matter is advantageous in that it provides an infusion management platform that provides a view on all infusions being administered to a patient that takes into account overfill/underfill practices of a particular care facility.

The details of one or more variations of the subject matter described herein are set forth in the accompanying drawings and the description below. Other features and advantages of the subject matter described herein will be apparent from the description and drawings, and from the claims.

DETAILED DESCRIPTION

Figure 1:
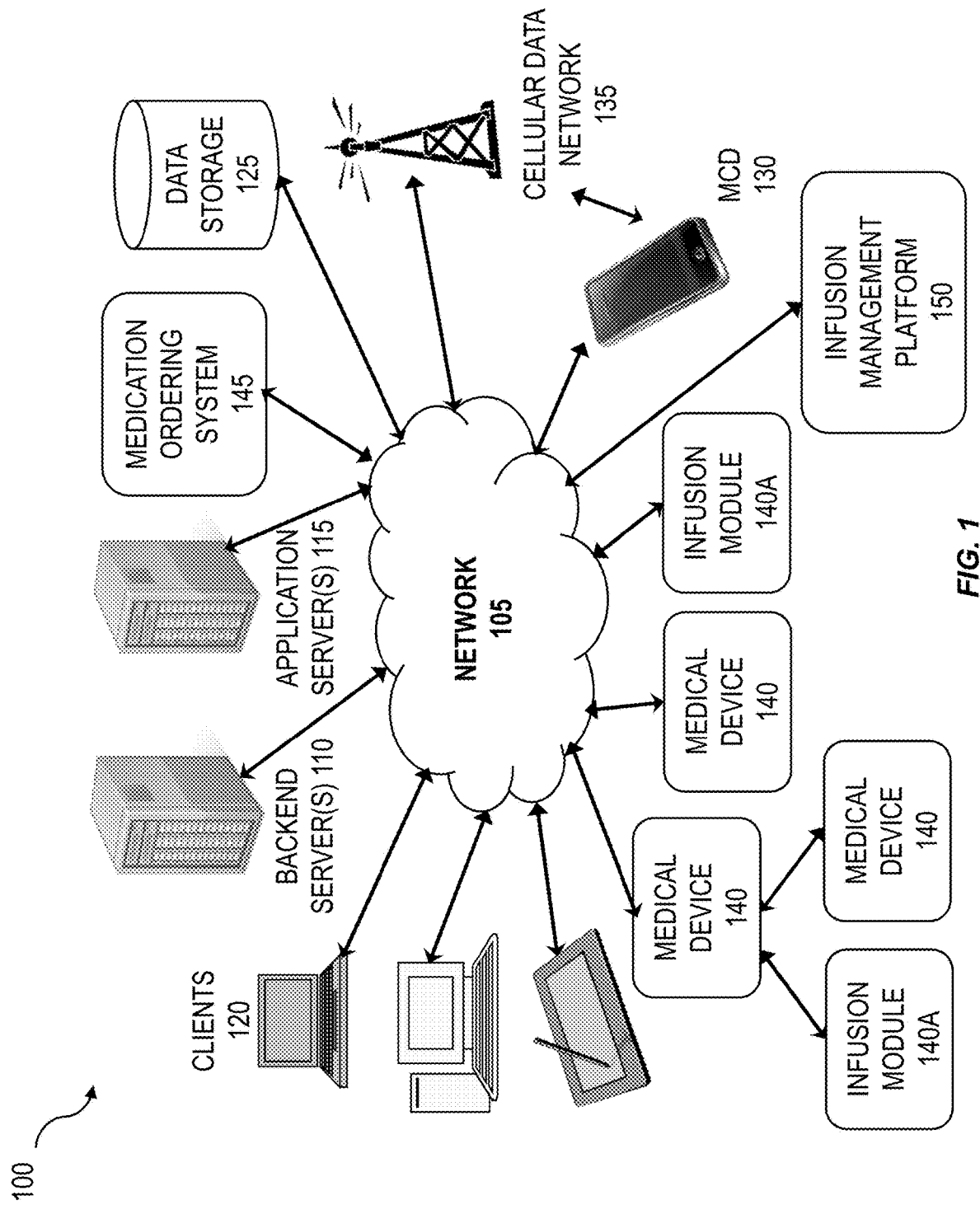
FIG. 1 is a system diagram illustrating a computing landscape within a healthcare environment.

FIG. 1 is a system diagram illustrating a computing landscape 100 within a healthcare environment such as a hospital. Various devices and systems, both local to the healthcare environment and remote from the healthcare environment, can interact via at least one computing network 105. This computing network 105 can provide any form or medium of digital communication connectivity (i.e., wired or wireless) amongst the various devices and systems. Examples of communication networks include a local area network ("LAN"), a wide area network ("WAN"), and the Internet. In some cases, one or more of the various devices and systems can interact directly via peer-to-peer coupling (either via a hardwired connection or via a wireless protocol such as Bluetooth or WiFi). In addition, in some variations, one or more of the devices and systems communicate via a cellular data network.

In particular, aspects of the computing landscape 100 can be implemented in a computing system that includes a back-end component (e.g., as a data server 110), or that includes a middleware component (e.g., an application server 115), or that includes a front-end component (e.g., a client computer 120 having a graphical user interface or a Web browser through which a user may interact with an implementation of the subject matter described herein), or any combination of such back-end, middleware, or front-end components. A client 120 and server 110, 115 are generally remote from each other and typically interact through the communications network 105. The relationship of the clients 120 and servers 110, 115 arises by virtue of computer programs running on the respective computers and having a client-server relationship to each other. Clients 120 can be any of a variety of computing platforms that include local applications for providing various functionality within the healthcare environment. Example clients 120 include, but are not limited to, desktop computers, laptop computers, tablets, and other computers with touch-screen interfaces. The local applications can be self-contained in that they do not require network connectivity and/or they can interact with one or more of the servers 110, 115 (e.g., a web browser).

A variety of applications can be executed on the various devices and systems within the computing landscape such as electronic health record applications, medical device monitoring, operation, and maintenance applications, scheduling applications, billing applications and the like.

The network 105 can be coupled to one or more data storage systems 125. The data storage systems 125 can include databases providing physical data storage within the healthcare environment or within a dedicated facility. In addition, or in the alternative, the data storage systems 125 can include cloud-based systems providing remote storage of data in, for example, a multi-tenant computing environment. The data storage systems 125 can also comprise non-transitory computer readable media.

Mobile communications devices (MCDs) 130 can also form part of the computing landscape 100. The MCDs 130 can communicate directly via the network 105 and/or they can communicate with the network 105 via an intermediate network such as a cellular data network. Various types of communication protocols can be used by the MCDs 130 including, for example, messaging protocols such as SMS and MMS.

Various types of medical devices 140 can be used as part of the computing landscape 100. For example, the landscape can include comprise various systems/units for delivering fluid (including medication) to a patient. On particular type of medical device 140 is an infusion module 140A. The infusion modules 140A can include various types of infusion pumps including peristaltic infusion pumps, large volume infusion pumps, and syringe pumps. The infusion modules 140A can be directly coupled to the network 105 and/or they can be coupled to a medical device 140 which is, in turn, coupled to the network 140.

The medical devices 140 can comprise, unless otherwise specified, any type of device or system with a communications interface that characterizes one or more physiological measurements of a patient and/or that characterize treatment of a patient. In some cases, the medical devices 140 communicate via peer to peer wired or wireless communications with another medical device 140 (as opposed to communicating with the network 105). For example, the medical device 140 can comprise a bedside vital signs monitor that is connected to other medical devices 140, namely a wireless pulse oximeter and to a wired blood pressure monitor. One or more operational parameters of the medical devices 140 can be locally controlled by a clinician, controlled via a clinician via the network 105, and/or they can be controlled by one or more of a server 115, 120, a client 125, a MCD 130, and/or another medical device 140.

The computing landscape 100 can provide various types of functionality as may be required within a healthcare environment such as a hospital. For the medical devices 140 can provide data characterizing one or more physiological measurements of a patient and/or treatment of a patient (e.g., medical device 140 can be an infusion management system, etc.). The data generated by the medical devices 140 can be communicated to other medical devices 140, the servers 110, 115, the clients 120, the MCDs 130, and/or stored in the data storage systems 125.

The computing landscape 100 can also include at least one medication ordering system 145. The medication ordering system 145 is coupled to the network and enables orders (e.g., prescriptions, etc.) to be generated and monitored. The medication order system 145 can be accessed, for example, via the one of the clients 120 and MCDs 130 via the application server 115. The medication ordering system 145 can specify a plurality of medications and/or other fluids to be infused into a patient over a pre-defined period of time and according to a pre-defined sequence via at least one infusion module 140A. These orders can be stored in the data storage 125 and/or pushed out to other clients 120, an MCD 130, and/or one or more of the medical devices 140. In some cases, caregivers alter the timing and sequence of such medication delivery based on reactions from the patient (as measured by various physiological sensors, etc.).

One more of the medical devices 140 (such as infusion modules 140A) can monitor an amount of fluid (e.g., medication, etc.) delivered to a patient. Fluids delivered to patients are referred to herein as infusions. Unless otherwise specified, references herein to medications should also be construed to include non-medication fluids (e.g., blood, saline, etc.) for delivery to a patient via an infusion module 140A.

As noted above, containers housing fluids such as medication often vary from the volumes ordered by a pharmacist/prescriber. A software-implemented infusion management platform 150 can be provided that includes a graphical user interface for tracking and monitoring infusions for one or more patients. The infusion management platform 150 communicates with the infusion modules 140A via the network 105. The infusion modules 140A can directly or indirectly provide various attributes relating to a particular infusion to the infusion management platform 150 (e.g., patient identifier, medication container identifier, medication type, rate of medication administration, infusion module identifier, etc.). Such attributes can be provided, for example, via messages sent from the infusion modules 140A. In some cases, the infusion management platform 150 receives medication orders from the medication ordering system 145 and then associates such orders with particular infusion modules 140A and/or particular patients (who are later associated with the infusion modules 140A).

An infusion sequence (which can be monitored by the infusion management platform 150) is a sequence of events that can include an infusion start, an infusion stop or complete, and all events that happened in-between (alarms, pause, re-starts, etc). The various events can be grouped together by the infusion management platform 150 (or alternatively on the infusion module 140A) under as single order identification (ID). The order ID can be provided by a hospital/facility via, for example, barcode or RIVO or it can be self-generated (e.g., PCU serial number+incremental counter) by the infusion management platform 150 in scenarios in which bar codes are not used.

The following describes how an order ID can be assigned for an infusion by the infusion management platform 150. Every infusion can have an order ID. If the volume to be infused (VTBI) as part of an infusion is changed, a new order ID can be assigned. If the drug that is being infused is changed, a new order ID can be assigned. If the medication container (e.g., syringe, etc.) for an infusion is changed, a new order ID can be assigned. In addition, infusions that are stopped and then restored/resumed, should use the original order ID.

Figure 2:
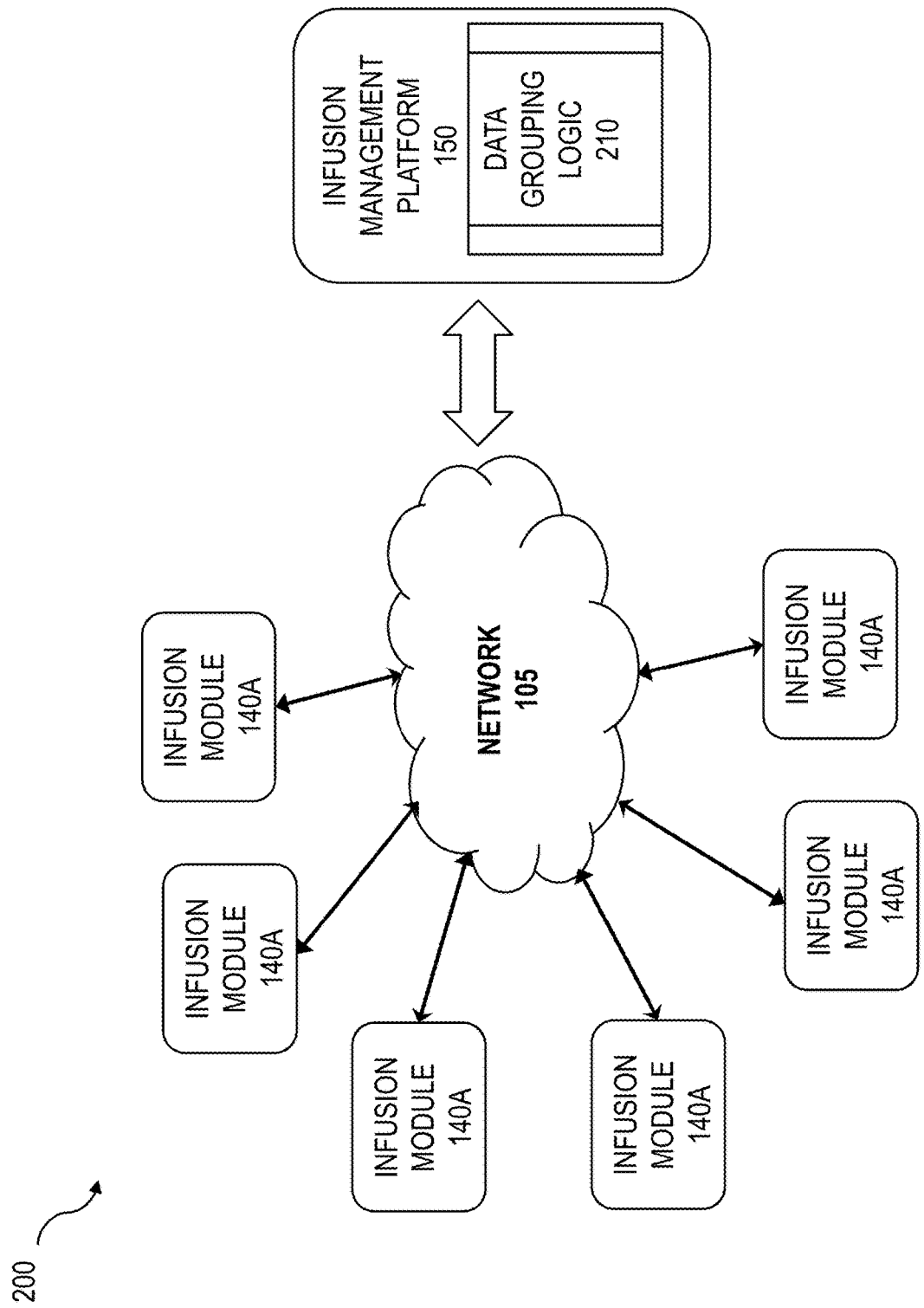
FIG. 2 is a system diagram illustrating interaction among an infusion management platform and numerous infusion modules.

FIG. 2 is a diagram 200 showing a different view of FIG. 1 in which the infusion modules 140A are connected to the infusion management platform 150 (either directly or indirectly as described above) via the network 105. The infusion management platform 150 comprises data grouping logic 210 that includes a set of rules (at least some of which are user configurable) that define how the infusion events are grouped based on the data generated by the infusion modules 140A. The data grouping logic 210 can be incorporated into the infusion management platform 150 and/or it can be remote and accessed via a web service by the infusion management platform 150.

Changes in VTBI do not necessarily constitute a start of a new infusion. If a drug or fluid is left in the bag, a clinician will enter a new VTBI to complete the residual drug or fluid. With most conventional infusion systems, entering a new VTBI will result in a new order ID assignment, although this is not a new infusion. The current subject matter addresses such issues by grouping infusions (using for example the data grouping logic 210) based on their start and end state.

In some implementations, the infusion management platform 150, can group infusions with system generated order ID using the data grouping logic 210. Infusions with and order ID provided by a hospital (via barcode or RIVO) can be grouped based on the order ID.

Figure 3:
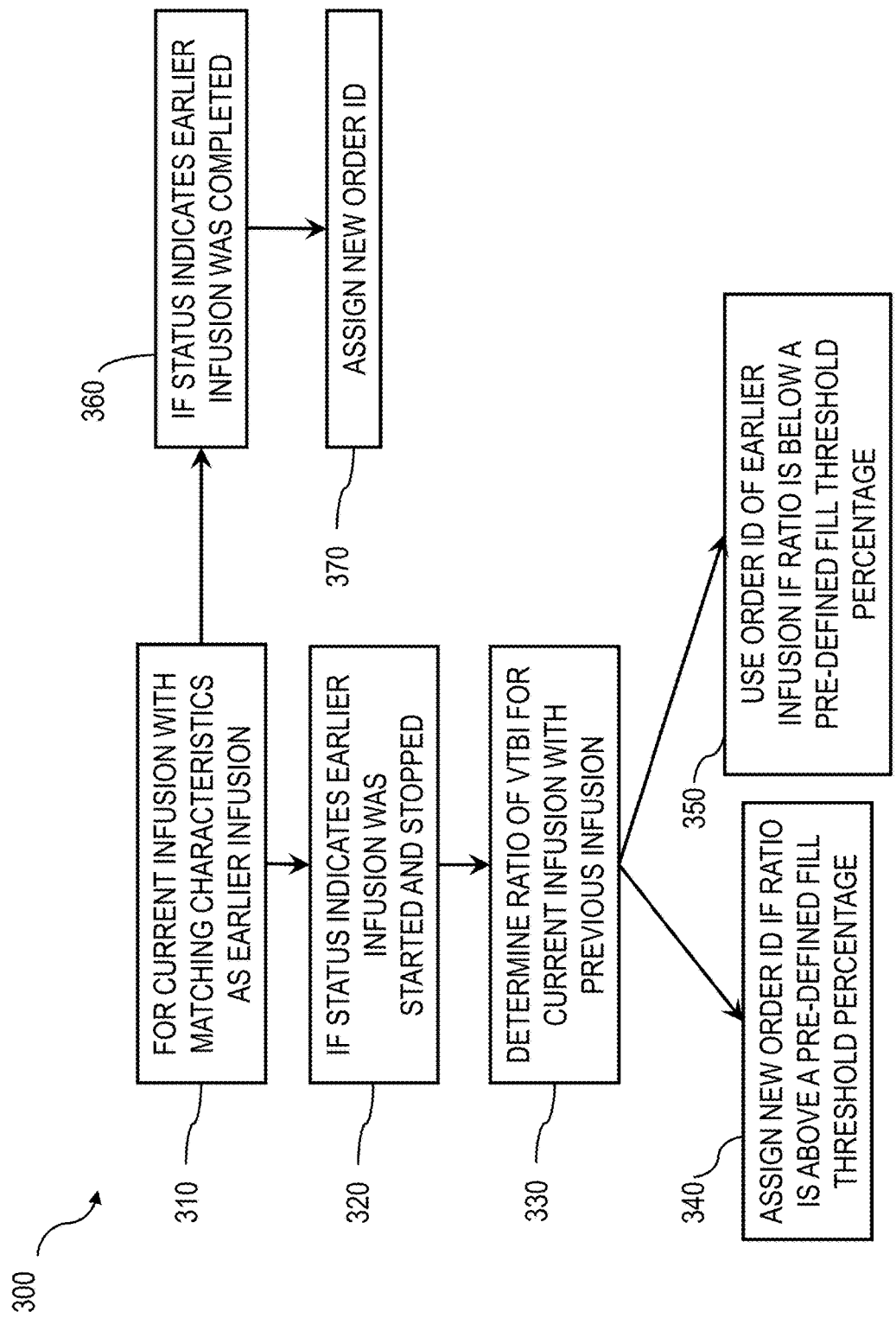
FIG. 3 is a first process flow diagram relating to assignment of infusion order identifiers.

With reference to the diagram 300 of FIG. 3, an infusion sequence can be grouped based on an infusion profile. The infusion profile can be based on one or more of: drug name, patient ID, infusion type, PCU serial number, and device module number and such information can be sent to the infusion management platform 150 from one or more of the infusion modules 140A. It can be determined, at 310, whether a current infusion has any of the same characteristics as an earlier infusion. For example, the determination can be made if current infusion has the same drug name, patient ID, infusion type, PCU serial number, and infusion module serial number. Not all of the profile information may needed in order to make the comparison. For example, infusion module serial can take priority followed by PCU serial number and infusion type if patient ID and drug name are not available.

Various types of state information can be made available regarding the earlier infusion. For example, state information can indicate that an earlier infusion was stopped and started (but not completed). This state information can be obtained via reason codes from the infusion modules 140A. The reason codes can indicate, for example, that the infusion was started and stopped.

A ratio of a volume to be infused (VTBI) for the current infusion as compared to the volume infused by the previous infusion can, at 330, be determined. A new order ID can be assigned, at 340, if the ratio is above a pre-defined fill threshold percentage. For example, if the VTBI for the current infusion exceeds 20% of the previous infusion infused volume. Otherwise, at 350, the order ID for the earlier infusion can be used if the ratio is below a pre-defined fill threshold percentage. If, at 360, the status indicates that the earlier infusion was completed (as opposed to stopped), then, at 370, a new order ID can be assigned for the current infusion.

In some cases, the pre-defined fill threshold percentage. For example, the percentage can be changed from 20% to 15%. In such cases, historical infusion data can be retrospectively analyzed and new order IDs assigned where warranted.

Various types of events can be used to update the status to indicate that an earlier infusion was completed. There can be explicit reason codes specifying one or more of infusion program completed, powered down, and new infusion initiated. Similarly, various types of events can be used to update the status to indicate that an earlier infusion was not completed. For example, there can be explicit reason codes that suggest that the infusion program was not completed such as alarm states, infusion program paused, infusion program restarted, and infusion program transitioned.

Figure 4:
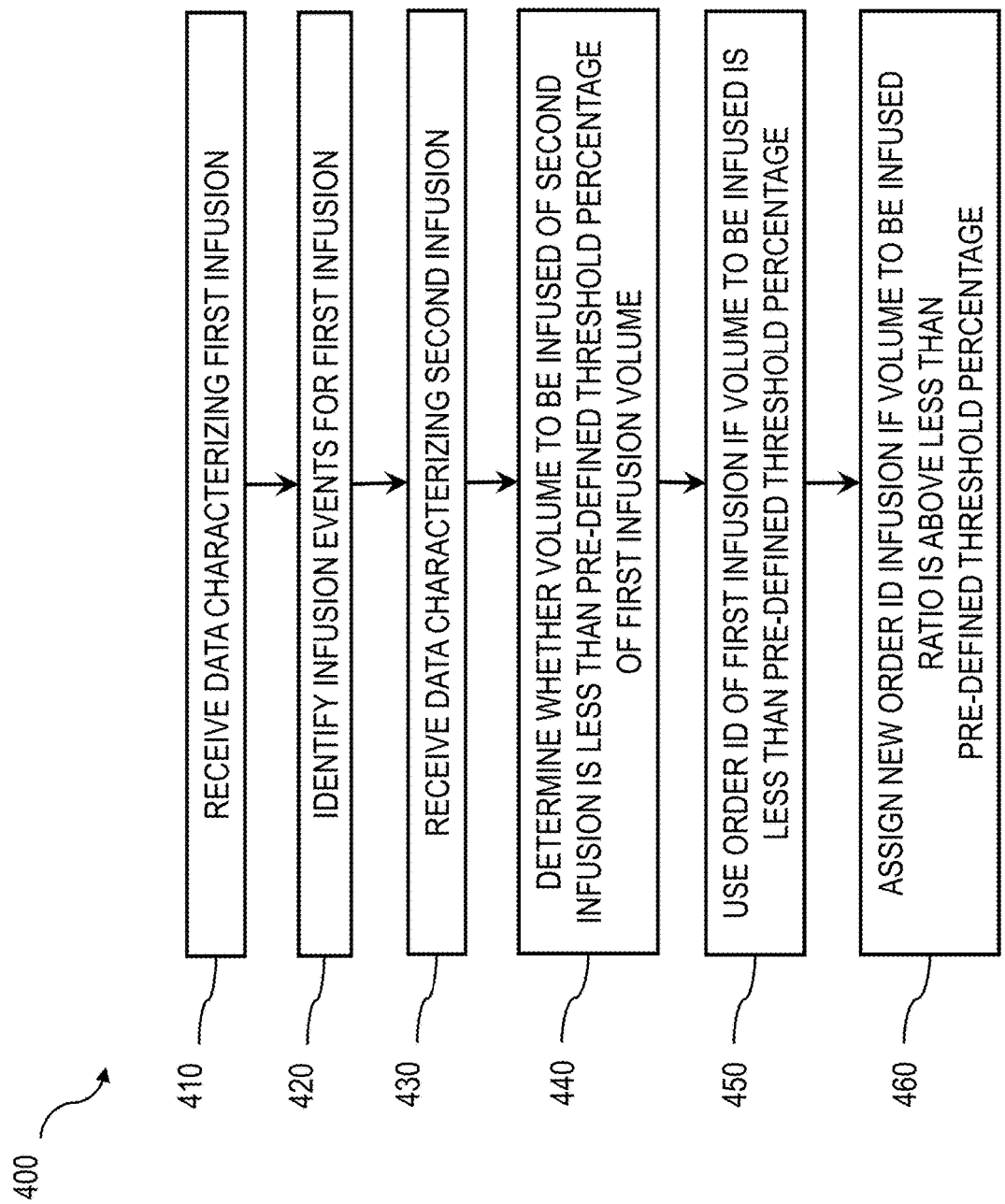
FIG. 4 is a second process flow diagram relating to assignment of infusion order identifiers.

FIG. 4 is a process flow diagram 400 in which at, 410, data is received that characterizes a first infusion of fluid into a patient from a container by an infusion module. The first infusion can have an associated first order identifier and an associated first volume infused. Thereafter, at 420, an infusion event can be identified interrupting or terminating the infusion. Subsequently, at 430, data is received that characterizes a second infusion of fluid into the patient by the infusion module. The second infusion can have an associated second volume to be infused. It can then, at 440, be determined whether the second volume to be infused is less than a pre-defined percentage of the first volume infused. The first order identifier can be assigned, at 450, to the second infusion if the second volume to be infused is less than a pre-defined percentage of the first volume infused. A second order identifier can be assigned, at 460, that is different from the first order identifier, if the second volume to be infused is greater than a pre-defined percentage of the first volume to be infused.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

What is claimed is:

1. A computer-implemented method, comprising:
    receiving, by at least one data processor, a first value for a parameter for a first delivery of fluid to a patient by a medical device, the first delivery having an associated first order identifier;
    identifying, by the at least one data processor, an event interrupting or terminating the first delivery of fluid to the patient;
    receiving, by the at least one data processor, a second value for the parameter for a second delivery of fluid to the patient by the medical device;
    determining, by the at least one data processor, that the second value differs from the first value by a pre-defined amount;
    assigning, by the at least one data processor, the first order identifier to the second delivery; and
    causing, by the at least one data processor, the medical device to deliver fluid to the patient using the second value of the parameter.

2. The computer-implemented method of claim 1, wherein information about the first delivery is associated with the first order identifier.

3. The computer-implemented method of claim 1, wherein the assignment of the first order identifier to the second delivery is in response to the determination that the second value differs from the first value by the predefined amount.

4. The computer-implemented method of claim 1, wherein the parameter comprises a volume of fluid to be infused.

5. The computer-implemented method of claim 1, wherein the pre-defined amount comprises a percentage of the first value for the parameter for the first fluid delivery.

6. The computer-implemented method of claim 1, further comprising:
    determining, by the at least one data processor, that first characteristics associated with the first delivery of fluid match second characteristics associated with the second delivery of fluid;
    wherein the assignment of the first order identifier to the second delivery is further in response to the determination that the first characteristics match the second characteristics.

7. The computer-implemented method of claim 6, wherein the first characteristics and the second characteristics comprise one or more of a profile name, a patient name, a medical device identifier, a patient care unit identifier, an infusion type, and a drug name.

8. A non-transitory computer-readable medium containing instructions which, when executed by at least one data processor, result in operations comprising:
    receiving a first value for a parameter for a first delivery of fluid to a patient by a medical device, the first delivery having an associated first order identifier;
    identifying an event interrupting or terminating the first delivery of fluid to the patient;
    receiving a second value for the parameter for a second delivery of fluid to the patient by the medical device;

determining that the second value differs from the first value by a pre-defined amount;
assigning the first order identifier to the second delivery; and
causing the medical device to deliver fluid to the patient using the second value of the parameter.

9. The non-transitory computer-readable medium of claim 8, wherein information about the first delivery is associated with the first order identifier.

10. The non-transitory computer-readable medium of claim 8, wherein the assignment of the first order identifier to the second delivery is in response to the determination that the second value differs from the first value by the predefined amount.

11. The non-transitory computer-readable medium of claim 8, wherein the parameter comprises a volume of fluid to be infused.

12. The non-transitory computer-readable medium of claim 8, wherein the pre-defined amount comprises a percentage of the first value for the parameter for the first fluid delivery.

13. The non-transitory computer-readable medium of claim 8, the operations further comprising:
determining that first characteristics associated with the first delivery of fluid match second characteristics associated with the second delivery of fluid;
wherein the assignment of the first order identifier to the second delivery is further in response to the determination that the first characteristics match the second characteristics.

14. The non-transitory computer-readable medium of claim 13, wherein the first characteristics and the second characteristics comprise one or more of a profile name, a patient name, a medical device identifier, a patient care unit identifier, an infusion type, and a drug name.

15. A system comprising:
at least one processor; and
a memory, wherein the at least one processor and the memory are configured to perform operations comprising:
receiving a first value for a parameter for a first delivery of fluid to a patient by a medical device, the first delivery having an associated first order identifier;
identifying an event interrupting or terminating the first delivery of fluid to the patient;
receiving a second value for the parameter for a second delivery of fluid to the patient by the medical device;
determining that the second value differs from the first value by a pre-defined amount;
assigning the first order identifier to the second delivery; and
causing the medical device to deliver fluid to the patient using the second value of the parameter.

16. The system of claim 15, wherein information about the first delivery is associated with the first order identifier.

17. The system of claim 15, wherein the assignment of the first order identifier to the second delivery is in response to the determination that the second value differs from the first value by the predefined amount.

18. The system of claim 15, wherein the parameter comprises a volume of fluid to be infused.

19. The system of claim 15, wherein the pre-defined amount comprises a percentage of the first value for the parameter for the first fluid delivery.

20. The system of claim 15, the operations further comprising:
determining that first characteristics associated with the first delivery of fluid match second characteristics associated with the second delivery of fluid;
wherein the assignment of the first order identifier to the second delivery is further in response to the determination that the first characteristics match the second characteristics.

* * * * *